US009274235B2

(12) United States Patent
Kang et al.

(10) Patent No.: US 9,274,235 B2
(45) Date of Patent: Mar. 1, 2016

(54) METHOD AND APPARATUS OF GENERATING X-RAY IMAGE

(71) Applicant: Samsung Electronics Co., Ltd., Suwon-si (KR)

(72) Inventors: Dong Goo Kang, Suwon-si (KR); Sung Hoon Kang, Suwon-si (KR); Young Hun Sung, Hwaseong-si (KR); Hyun Hwa Oh, Hwaseong-si (KR); Myung Jin Chung, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 160 days.

(21) Appl. No.: 14/069,975

(22) Filed: Nov. 1, 2013

(65) Prior Publication Data
US 2014/0185759 A1 Jul. 3, 2014

(30) Foreign Application Priority Data

Dec. 27, 2012 (KR) .......................... 10-2012-0154936

(51) Int. Cl.
| G01N 23/00 | (2006.01) |
| G01T 1/20 | (2006.01) |
| G01N 23/04 | (2006.01) |
| A61B 6/00 | (2006.01) |
| G21K 1/10 | (2006.01) |

(52) U.S. Cl.
CPC .............. *G01T 1/2018* (2013.01); *A61B 6/4241* (2013.01); *A61B 6/482* (2013.01); *A61B 6/5205* (2013.01); *G01N 23/04* (2013.01); *A61B 6/4291* (2013.01); *A61B 6/502* (2013.01); *G21K 1/10* (2013.01)

(58) Field of Classification Search
CPC .... G01T 1/2018; A61B 6/482; A61B 6/5205; A61B 6/4241; A61B 6/502; A61B 6/4291; G01N 23/04; G21K 1/10
USPC ........................................................ 378/98.12
See application file for complete search history.

(56) References Cited

U.S. PATENT DOCUMENTS

| 6,683,934 B1 * | 1/2004 | Zhao ...................... A61B 6/032 |
| | | 378/37 |
| 7,724,874 B2 * | 5/2010 | Kameshima .......... G01T 1/2018 |
| | | 250/370.09 |

(Continued)

FOREIGN PATENT DOCUMENTS

| JP | 2000-98536 | 4/2000 |
| JP | 2008-516692 | 5/2008 |

(Continued)

*Primary Examiner* — Michael Maskell
(74) *Attorney, Agent, or Firm* — NSIP Law

(57) ABSTRACT

Disclosed herein are an X-ray detection panel, an X-ray image generating module, an X-ray imaging apparatus, and a method of generating an X-ray image. The X-ray imaging apparatus includes an X-ray generator configured to emit X-rays; an X-ray detection panel comprising a plurality of pixel groups, each pixel group configured to detect X-rays having an energy band and to convert the detected X-rays into electrical signals; and an image processor configured to acquire readout data from the electrical signals of at least one of the plurality of pixel groups, to calculate estimated data, and to generate an X-ray image by combining the readout data and the estimated data.

22 Claims, 22 Drawing Sheets

(56) References Cited

U.S. PATENT DOCUMENTS

| | | | |
|---|---|---|---|
| 2008/0260092 A1* | 10/2008 | Imai | A61B 6/032 378/5 |
| 2011/0188723 A1* | 8/2011 | Bruder | A61B 6/032 382/131 |
| 2012/0236987 A1* | 9/2012 | Ruimi | A61B 6/032 378/19 |
| 2012/0288062 A1* | 11/2012 | Takasaki | A61B 6/542 378/62 |
| 2012/0301002 A1* | 11/2012 | Flohr | A61B 6/032 382/131 |
| 2014/0185752 A1* | 7/2014 | Lu | A61B 6/4035 378/53 |

FOREIGN PATENT DOCUMENTS

| | | |
|---|---|---|
| JP | 2008-272202 | 11/2008 |
| JP | 2011-19591 | 2/2011 |

* cited by examiner

METHOD AND APPARATUS OF GENERATING X-RAY IMAGE

CROSS-REFERENCE TO RELATED APPLICATION

This application claims the benefit under 35 U.S.C. §119(a) of Korean Patent Application No. 2012-0154936, filed on Dec. 27, 2012 in the Korean Intellectual Property Office, the entire disclosure of which is incorporated herein by reference for all purposes.

BACKGROUND

1. Field

The following description relates to an X-ray imaging apparatus and a method of generating an X-ray image.

2. Description of the Related Art

X-ray imaging apparatuses are devices that irradiate an object, for example, a human body, with X-rays having a predetermine energy band, detects X-rays that have passed through the object, and acquires an image from the X-rays. Accordingly, an X-ray image of the inside of the object, for example, internal parts of the human body, may be acquired. X-ray imaging has been widely applied to various fields, such as, for example, medical diagnosis and baggage screening because it is possible to nondestructively inspect the internal structure of an object.

The X-ray imaging apparatus may obtain the internal structure of an object based on difference in X-ray absorbance of internal parts of the object. When an object is irradiated with X-rays, tissues having a higher X-ray absorbance among the internal tissues absorb most of the X-rays, and tissues having a lower X-ray absorbance transmit most of the X-rays. An X-ray detector detects the transmitted X-rays, and an X-ray image is generated according to the detected X-rays, thereby detecting the internal tissues of the object.

Types of detectable tissues vary according to the energy band of the emitted X-rays. For example, hard tissues such as bones may be detected when an object, for example, a human body, is irradiated with high energy band X-rays. On the other hand, when the object is irradiated with low energy band X-rays, transmittance of the X-rays through the internal tissues of the object decreases, thereby enabling detection of soft tissues. Thus, full field digital mammography (FFDM) may detect abnormalities of a breast by irradiating the breast with low energy band X-rays.

A multi-energy X-ray (MEX) image is an X-ray image used to inspect and confirm various tissues inside an object by taking images of the object plural times using X-rays having various energy bands. In order to obtain the multi-energy X-ray image, a method of exposing the object sequentially to X-rays having different energy bands has been used and X-ray photons may be detected through charge integration. However, this method exposes the object to X-rays plural times.

Alternatively, the multi-energy X-ray image may be acquired by converting single X-ray photons into electrical signals using a photon counting detector and attenuating amplitudes of the electrical signals by use of proportional relationship between the amplitudes of the converted electrical signals and energy. In the latter case, the multi-energy X-ray image may be acquired by use of a single stage of X-ray irradiation. However, this method has not been commercialized due to difficulties in the manufacturing process.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided an X-ray imaging apparatus including an X-ray generator configured to emit X-rays; an X-ray detection panel comprising a plurality of pixel groups, each pixel group configured to detect X-rays having an energy band and to convert the detected X-rays into electrical signals; and an image processor configured to acquire readout data from the electrical signals of at least one of the plurality of pixel groups, to calculate estimated data, and to generate an X-ray image by combining the readout data and the estimated data.

The image processor may be configured to acquires an image having a high contrast to noise rate (CNR) by adding a weight to the generated X-ray image.

The image processor may be configured to generate a plurality of X-ray images corresponding to the electrical signals of a plurality of pixel groups.

The image processor may be configured to generate energy subtraction X-ray images by applying energy subtraction to the plurality of X-ray images.

The image processor may be configured to generate a multi-energy X-ray image by combining the generated plurality of X-ray images.

The X-ray detection panel may further comprise a plurality of filters disposed on a surface of pixels of the pixel groups; the filters may be configured to adjust the energy band of the X-ray detected by the pixel groups; and the filters disposed over pixels of the same pixel group may be configure to adjust the energy band by an identical amount.

The readout data may be image data for a first portion of the X-ray image and the estimated data may be image data for a second portion of the X-ray image.

In another general aspect, there is provided an X-ray detection panel comprising a plurality of pixel groups, each pixel group configured to detect X-rays having an energy band and to convert the detected X-rays into electrical signals; and an image processor configured to acquire readout data of a first portion of an X-ray image from the electrical signals of at least one of the plurality of pixel groups, to calculate estimated data of a second portion of the X-ray image based on the acquired readout data, and to generate the X-ray image having a single energy band by combining the readout data and the estimated data.

The image processor may be further configured to generate a color X-ray image by adding colors to the generated X-ray image.

The image processor is further configured to generate a contrast to noise rate (CNR) image having a high CNR by adding a weight to the generated X-ray image.

The image processor may be further configured to generate a plurality of X-ray images corresponding to X-rays detected by the plurality of pixel groups.

The image processor may be further configured to generate an energy subtraction X-ray image by applying energy subtraction to the plurality of X-ray images.

The image processor may be further configured to generate a multi-energy X-ray image by combining the generated plurality of X-ray images.

A plurality of filters may be connected to pixels of each of the pixel groups and may be configured to adjust energy bands of the X-rays.

The estimated data may be calculated based on the readout data through interpolation.

In another general aspect, there is provided a method of generating an X-ray image, the method including: detecting, at a plurality of pixel groups of an X-ray detection panel, X-rays having different energy bands; converting the detected X-rays into electrical signals; acquiring readout data of a first portion of an X-ray image from the electrical signals of one of the plurality of pixel groups; calculating estimated data of a second portion of the X-ray image based on the readout data; and combining the readout data and the estimated data to generate the X-ray image having a single energy band.

The method may include generating a color X-ray image by adding colors to the generated X-ray image.

The method may include generating a contrast to noise rate (CNR) image having a high CNR by adding a weight to the generated X-ray image.

The method may include generating a plurality of X-ray images by repeating the acquiring of the readout data, the calculating of the estimated data, and the combining the readout data and the estimated data for each of the X-rays detected by the plurality of pixel groups.

In another general aspect, there is provided an X-ray image generating apparatus including: an X-ray detection panel comprising a plurality of pixel groups, each pixel group configured to detect X-rays having an energy band and to convert the detected X-rays into electrical signals; a plurality of filters disposed on a surface of pixels of the pixel groups and the filters are configured to adjust the energy band of the X-ray detected by each pixel group by an identical amount; and an image processor configured to acquire readout data from the electrical signals of at least one of the plurality of pixel groups, to calculate estimated data, and to generate an X-ray image by combining the readout data and the estimated data.

The pixel groups may be sequentially disposed in the X-ray detection panel.

In another general aspect there is provided an X-ray image generating module capable of generating a plurality of X-ray images corresponding to X-rays having a plurality of energy bands detected using an X-ray detection panel that may simultaneously detect the X-rays having a plurality of energy bands, an X-ray imaging apparatus, and a method of generating a plurality of X-ray images using the same.

Other features and aspects will be apparent from the following detailed description, the drawings, and the claims.

Figure 1:
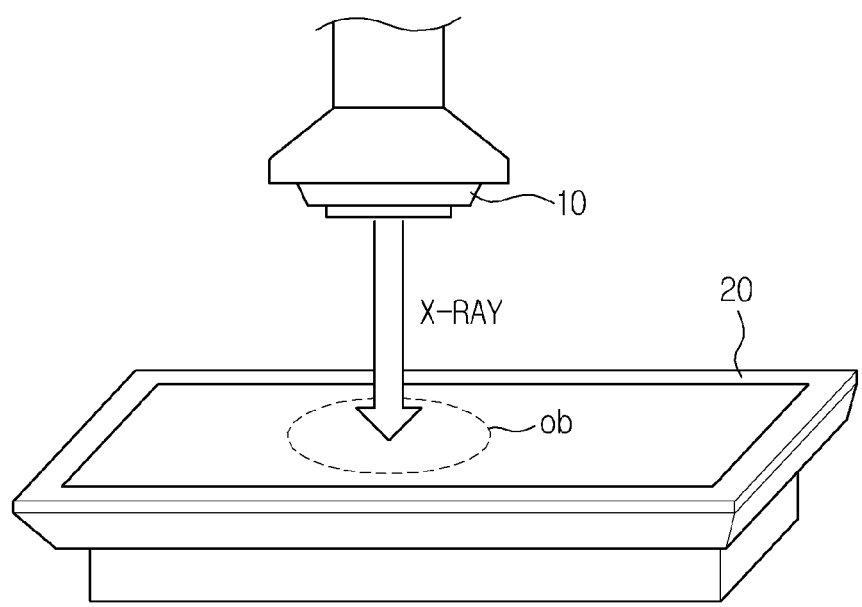
FIG. 1 is a diagram illustrating an example of an X-ray imaging apparatus.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be apparent to one of ordinary skill in the art. Also, descriptions of well-known functions and constructions may be omitted for increased clarity and conciseness.

FIG. 1 illustrates an example of an X-ray imaging apparatus. Only components related to the present example are illustrated in the X-ray imaging apparatus of FIG. 1. Thus, those skilled in the art may understand that general components except for components illustrated in FIG. 1 may be further included. For example, the X-ray imaging apparatus may include an interface unit (not illustrated). The interface unit may be responsible for inputting and outputting input information regarding a user and an image. The interface unit may include a network module for connection to a network and a universal serial bus (USB) host module for forming a data transfer channel with a mobile storage medium, depending on a function of the X-ray imaging. In addition, the interface unit includes an input/output device such as a mouse, a keyboard, a touch screen, a monitor, a speaker, and a software module for running the input/output device. In addition, the X-ray imaging apparatus may further include a storage unit (not illustrated) that stores models that are described below. The storage unit may include, for example, a hard disk drive (HDD), a read only memory (ROM), a random access memory (RAM), a flash memory, or a memory card as an ordinary storage medium.

Referring to FIG. 1, an X-ray imaging apparatus including an X-ray image generating module includes an X-ray generator 10 that generates X-rays and emits the X-rays to an object ob and an object support table 20 disposed at the opposite side of the X-ray generator 10 with respect to the object ob. The object ob is placed between the object support table 20 and the X-ray generator 10.

The X-ray generator 10 includes an X-ray tube that generates X-rays as electrons accelerated and discharged from a cathode in accordance with an applied voltage to collide with a counter electrode and an electric circuit that performs voltage transformation to apply a predetermined voltage to the X-ray tube. X-rays are generated having a predetermined energy band and are emitted to an object from the X-ray generator. The voltage applied to the X-ray tube determines the energy band of the X-rays emitted. X-rays having different energy bands indicate that there is at least one difference of the upper limit and the lower limit between the energy bands or there is a different mean or median value between the X-ray energy spectra.

Figure 2:
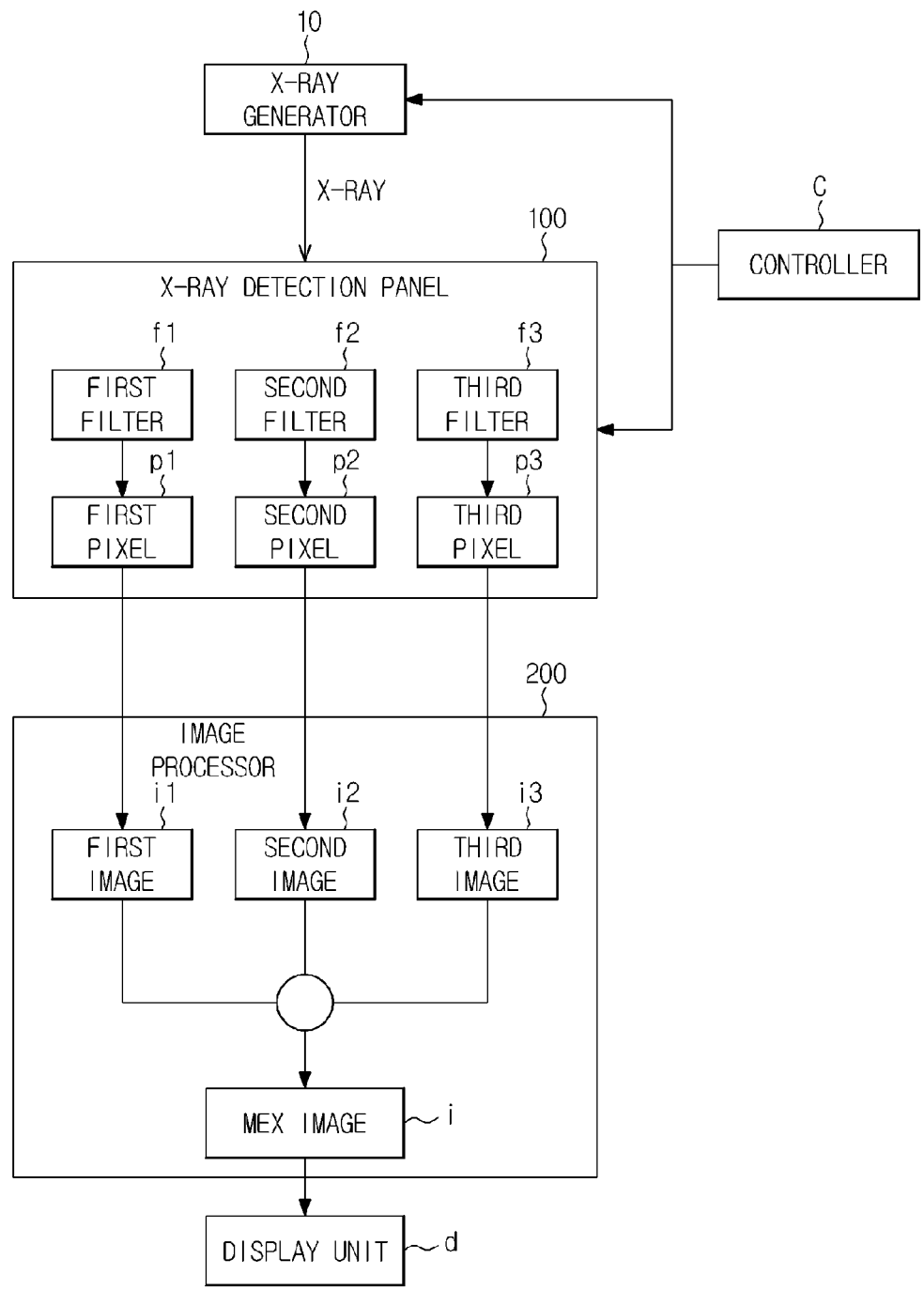
FIG. 2 is a diagram illustrating an example of an X-ray imaging apparatus.

An X-ray detection panel 100 of FIG. 2 is mounted at the object support table 20. The X-ray detection panel 100 detects X-rays emitted from the X-ray generator 10, which have passed through the object ob, and converts the received X-rays into electrical signals.

The X-ray imaging apparatus may be a full field digital mammography (FFEM) apparatus. The FFEM apparatus further includes a compression unit that compresses an object, i.e., a breast compression unit that compresses a breast, placed on the object support table 20. The breast compression unit expands the cross-sectional area of the breast in the image by compressing the breast. The FFEM apparatus also includes the X-ray detection panel 100 disposed under the object support table 20 to detect X-rays emitted from the X-ray generator 10.

FIG. 2 is a diagram illustrating an example of an X-ray imaging apparatus.

As illustrated in FIG. 2, the X-ray imaging apparatus includes an X-ray generator 10 generating X-rays, an X-ray detection panel 100 that receives irradiated X-rays and converts the received X-rays into electrical signals, and an image processor 200 that reads out an X-ray image from the electrical signals converted by the X-ray detection panel 100. The X-ray imaging apparatus may further include a display unit d that displays images generated by the image processor 200 and a controller c that controls the X-ray generator 10, the X-ray detection panel 100, the image processor 200, and the display unit d.

Figure 3:
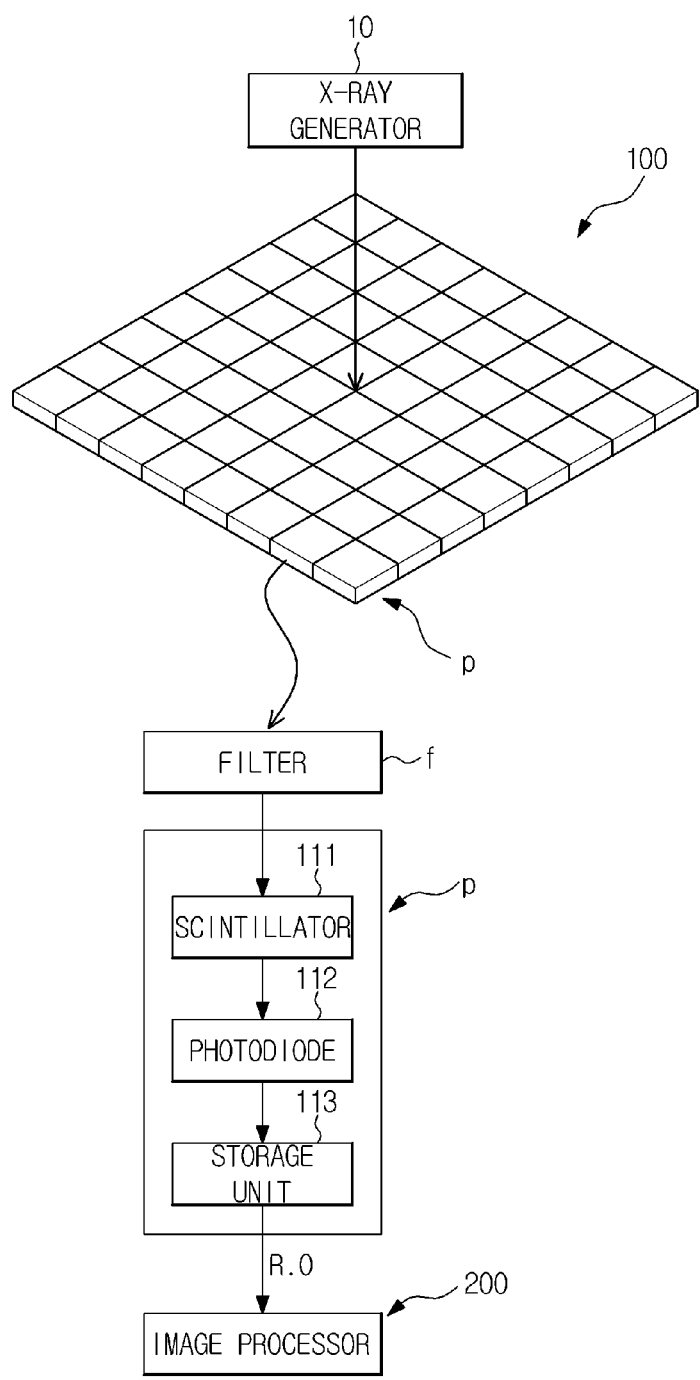
FIG. 3 is a diagram illustrating an example of an X-ray detection panel.

FIG. 3 is a diagram illustrating an example of an X-ray detection panel.

The X-ray detection panel 100 is an X-ray sensing device that receives X-rays, outputs electrical signals corresponding to the received X-rays, and stores the electrical signals. The X-ray detection panel 100 may be, for example, a charge integration-type flat panel detector or a photon counting detector. As illustrated in FIG. 3, the X-ray detection panel 100 may be divided into a plurality of pixels p. Each of the plurality of pixels p constituting the X-ray detection panel 100 receives X-rays that have passed through the object, converts the X-rays into electrical signals, outputs, and stores the electrical signals.

Each pixel p constituting the X-ray detection panel 100 includes a scintillator 111, a photodiode 112, and a storage unit 113.

The scintillator 111 absorbs photons of X-rays, converts the photons into visible light photons, and transfers the visible light photons to the photodiode 112. The photodiode 112 senses and absorbs the photons output from the scintillator 111 and converts the absorbed photons into electrical signals. The converted electrical signals are temporarily stored in the storage unit 113 such as, for example, a storage capacitor. The image processor 200 reads the electrical signals stored in the storage unit 113 to generate an X-ray image.

Although each of the pixels p detects X-rays having a predetermined energy band, all pixels p do not detect X-rays having the same energy band. Some pixels among the plurality of pixels p of the X-ray detection panel 100 may detect X-rays having an energy band that is the same as or different from that of other pixels. For example, some pixels of the X-ray detection panel 100 may detect X-rays of a low energy band, other pixels may detect X-rays of a medium energy band, and the other pixels may detect X-rays of a high energy band, to convert the X-rays into different electrical signals.

Thus, the electrical signals stored in the pixels p of the X-ray detection panel 100 may not be electrical signals converted from X-rays of the same energy band.

A group of pixels detecting X-rays having the same energy band among the pixels p of the X-ray detection panel 100 are referred to as pixel group g. Thus, each pixels belonging to one pixel group g detects X-rays having the same energy band. Likewise, pixels belonging to one pixel group g detect X-rays having an energy band different from that detected by pixels belonging to another pixel group g.

Filters f, which change the energy band of X-rays, may be installed at the front surface of the x-ray detection panel 100, i.e., at the front surfaces of the pixels p. The filter f may attenuate the energy band of emitted X-rays such that the energy band of X-rays detected by each pixel p becomes different from the energy band of X-rays emitted from the X-ray generator 10. As a non-exhaustive illustration only, the filters f installed at the front surfaces of the pixels p of the X-ray detection panel 100 may not attenuate the energy bands of the X-rays by the same amount. As another non-exhaustive illustration only, various types of filters f having different attenuation factors according to the positions of the pixels p on the X-ray detection panel 100 may be installed, such that the energy band of X-rays detected by some pixels p may be different from the energy band of X-rays detected by other pixels p. Thus, detectable energy bands of X-rays may be assigned to the pixels p. Accordingly, each pixel p detects X-rays having a predetermined energy band in accordance with the assigned energy band, and X-rays having the assigned energy band are converted into electrical signals by use of, for example, the scintillator 111 and the photodiode 112. The electrical signals are stored in the storage unit 113.

Filters f having the same attenuation factor may be installed at pixels p belonging to one pixel group g. In addition, filters f having an attenuation factor different from the above-mentioned attenuation factor may be installed at pixels p belonging to another pixel group. In other words, each pixel group g may be provided with different filters f. Thus, even when X-rays having the same energy band are irradiated to all pixel groups g of the X-ray detection panel 100, the pixel groups g may detect X-rays having different energy bands by use of the filters f having different attenuation factors and installed at each of the pixel groups g.

Figure 4:
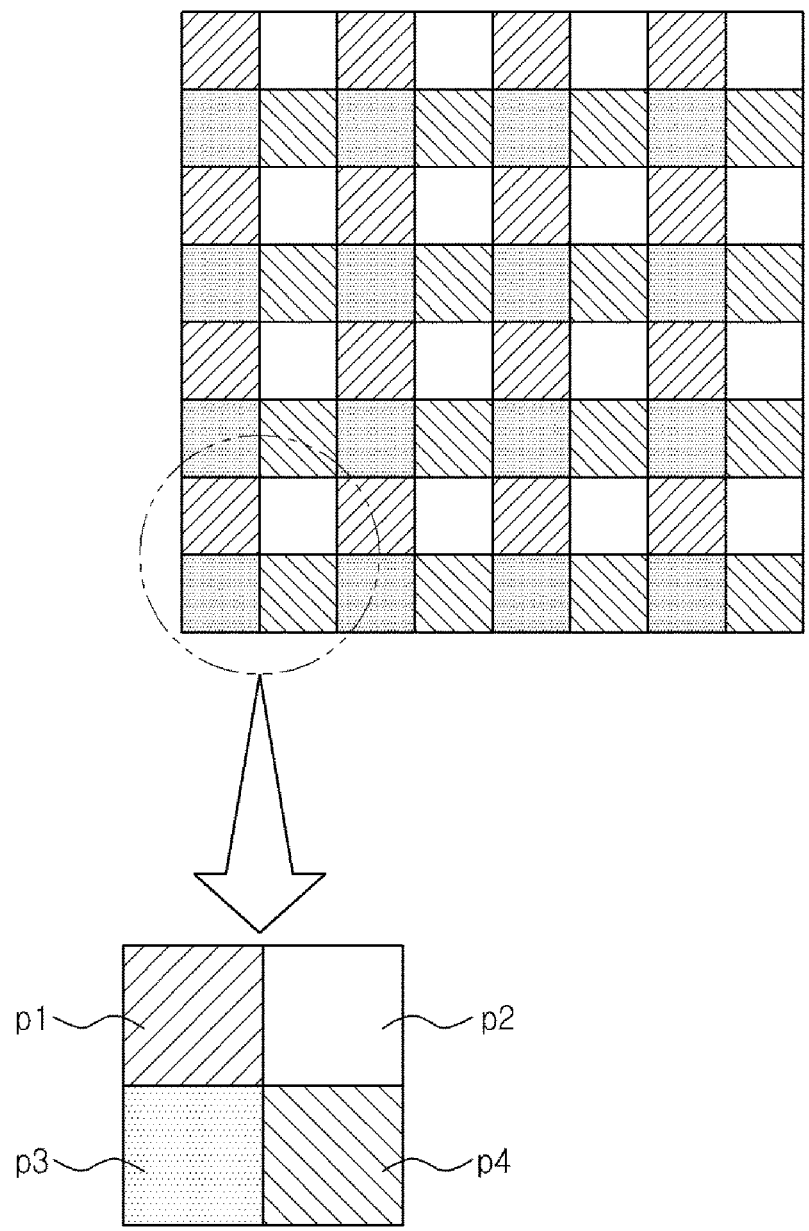
FIG. 4 is a diagram illustrating an example of an X-ray detection panel.

FIG. 4 is a diagram illustrating an example of an X-ray detection panel. As described above, the X-ray detection panel 100 may be divided into a plurality of pixels p. As illustrated in FIG. 4, a first pixel p1 may detect an X-ray having a first energy band, and a second pixel p2 may detect an X-ray having a second energy band. Thus, a first pixel group g1 includes a plurality of first pixels p1, and a second pixel group g2 includes a plurality of second pixels p2.

When X-rays to be detected have a range of energy bands, the X-ray detection panel 100 may include additional pixel groups. As another non-exhaustive illustration only, the X-ray detection panel 100 may include a third pixel group g3, including a plurality of third pixels p3, a fourth pixel group g4 including a plurality of fourth pixels p4, or more pixel groups in accordance with the X-rays to be detected. In this regard, the third pixel group g3 and the fourth pixel group g4 may detect X-rays having corresponding energy bands, for example, X-rays having a third energy band and a forth energy band as described above. The X-ray detection panel 100 may include the pixel groups, such as, for example, the first to fourth pixel groups g1 to g4, which detect X-rays having different energy bands according to characteristics of X-rays to be detected.

Thus, accordingly to a non-exhaustive example only, when the X-ray detection panel 100 is used to detect up to four types of X-rays, the X-ray detection panel 100 may include a plurality of pixel groups, i.e., the first to fourth pixel groups g1 to g4. Pixels of the pixel groups, g1 to g4, detecting X-rays having different energy bands, such as, for example, the first to fourth pixels p1 to p4, may be aligned on the X-ray detection panel 100 in a predetermined pattern. As a non-exhaustive example illustrated in FIG. 4, the pixels p1 to p4 may be arrayed at a region of the X-ray detection panel 100 in a matrix pattern. Referring to FIG. 4, the second pixels p2 are disposed at left and right sides of the first pixel p1, the third pixels p3 are disposed at upper and lower sides of the first pixel p1, and the fourth pixels p4 are disposed at upper and lower sides of the second pixel p2, i.e., at left and right sides of the third pixel p3. The first pixel to fourth pixels p1 to p4 detect and convert X-rays having different energy bands into electrical signals. Thus, the X-ray detection panel 100 may detect a plurality of X-rays having different energy bands, such as, for example, up to four X-rays in this case, using a plurality of the first pixel p1 to fourth pixels p4.

As described above, the pixels detecting X-rays having different energy bands may be arranged on the X-ray detection panel 100 in various other patterns. The X-ray detection panel 100 may include pixel areas, each including a plurality of pixels to detect X-rays having different energy bands and to convert the detected X-rays into electrical signals. As illustrated in the example of FIG. 4, a pixel area refers to an area including four pixels, first to fourth pixels p1 to p4, used to detect X-rays having different energy bands and aligned in a predetermined pattern. The X-ray detection panel 100 may include a plurality of pixel areas, each including a plurality of pixels.

Figure 5:
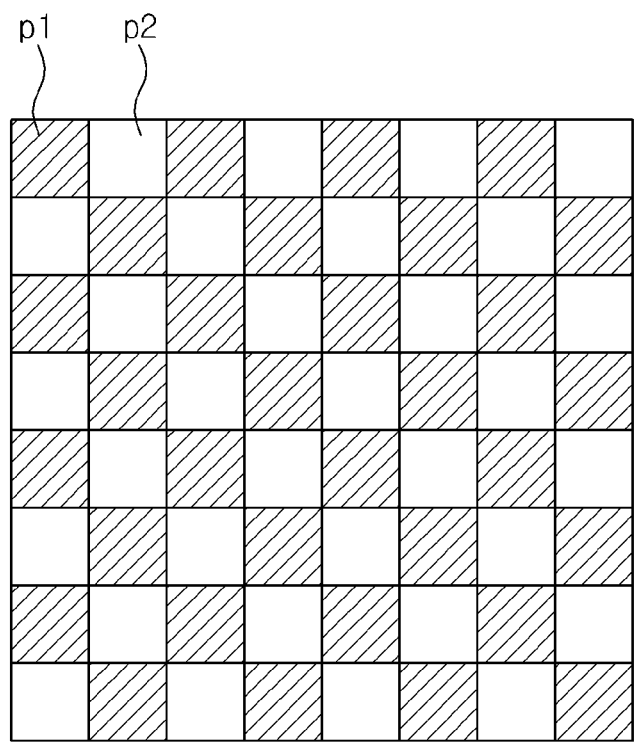
FIG. 5 is a diagram illustrating an example of an X-ray detection panel.

Other non-exhaustive examples of the X-ray detection panel will be described with reference to FIGS. 5 and 6. FIG. 5 is a diagram illustrating another example of the X-ray detection panel.

Referring to FIG. 5, the X-ray detection panel 100 may include a first pixel group g1 and a second pixel group g2 detecting X-rays having two different energy bands. As illustrated in FIG. 5, each of the plurality of first pixels p1 belonging to the first pixel group g1 and each of the plurality of second pixels p2 belonging to the second pixel group g2 may be alternately disposed on the X-ray detection panel 100. That is, the second pixels p2 may be disposed at four sides of each of the first pixels p1.

Figure 6:
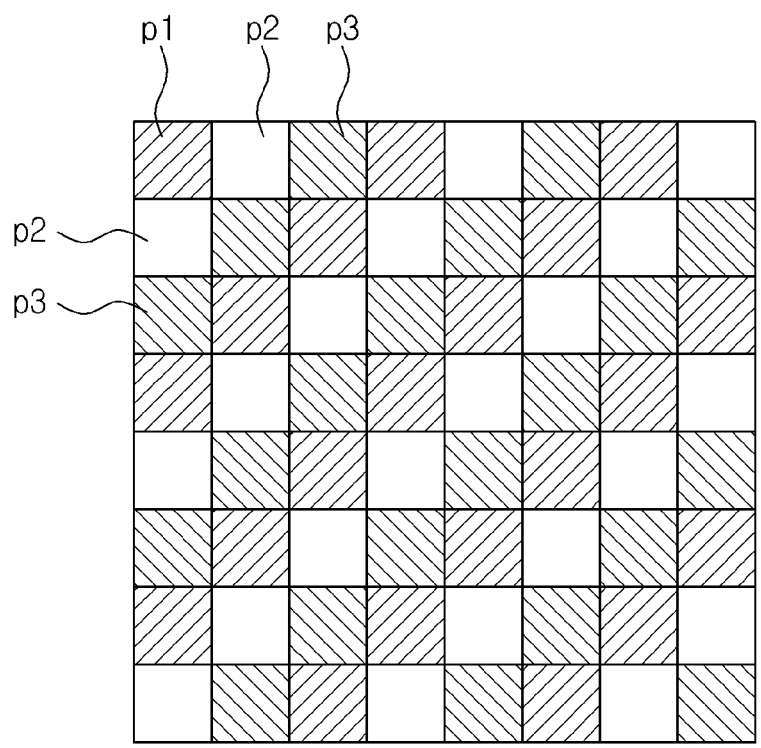
FIG. 6 is a diagram illustrating an example of an X-ray detection panel.

FIG. 6 is a diagram illustrating another example of an X-ray detection panel.

Referring to FIG. 6, the X-ray detection panel 100 may include a first pixel group g1, a second pixel group g2, and a third pixel group g3 detecting X-rays having three different energy bands. As illustrated in FIG. 6, each of a plurality of first pixels p1 belonging to the first pixel group g1, each of a plurality of second pixels p2 belonging to the second pixel group g2, and each of a plurality of third pixels p3 belonging to the third pixel group g3 may be sequentially disposed on the X-ray detection panel 100. The first to third pixels p1 to p3 may be aligned such that the second pixel p2 is disposed between the first pixel p1 and the third pixel p3 and this arrangement of pixels p1 to p3 is repeated.

In addition, as illustrated in FIG. 6, the first pixel p1 to the third pixel p3 may be sequentially aligned in a longitudinal direction as well as in a lateral direction. In the longitudinal direction, the second pixel p2 is disposed between the first pixel p1 and the third pixel p3 on the X-ray detection panel 100. As a non-exhaustive example only, the X-ray detection panel 100 may have a pattern of the plurality of pixels p of the plurality of pixel groups as described above. When the image processor 200, which will be described later, calculates estimated data from readout data through, for example, interpolation, estimated data may be efficiently calculated from the pixels p aligned in a predetermined pattern.

Figure 7A:
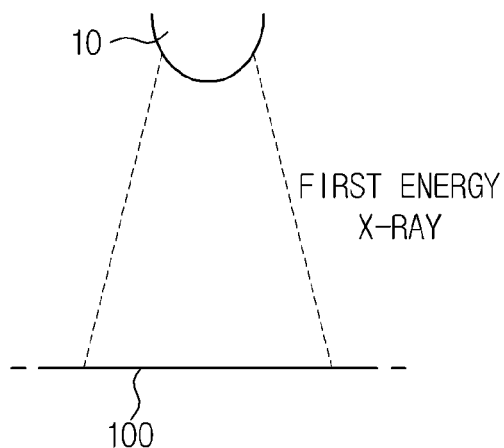
FIGS. 7A-7C are diagrams illustrating examples of an X-ray irradiation method to acquire X-ray images from a plurality of different energy bands.
Figure 7B:
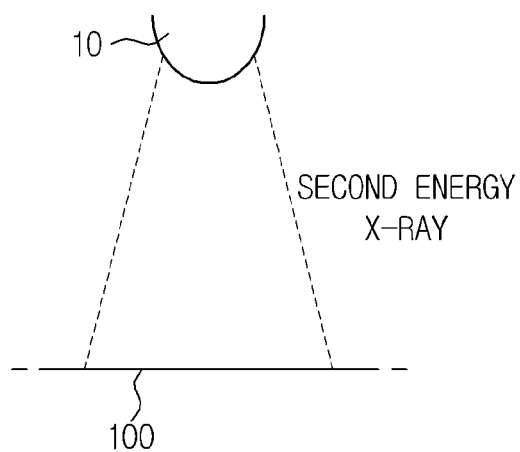
Figure 7C:
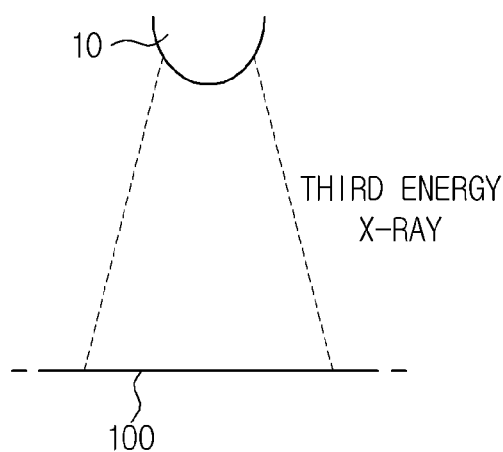

FIG. 7A-7C are diagrams illustrating examples for describing an X-ray irradiation. In order to obtain images from X-rays having different energy levels, the X-ray generator 10 sequentially irradiates X-rays having different energy levels, e.g., X-rays having first to third energy bands to the X-ray detection panel 100 as illustrated in FIGS. 7A to 7C. The X-ray detection panel 100 receives the X-rays having different energy levels and produces electrical signals to form a plurality of X-ray images.

Figure 8:
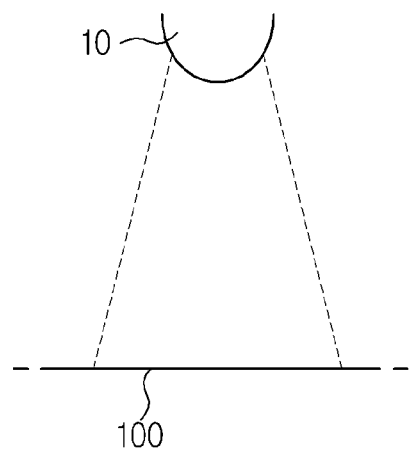
FIG. 8 is a diagram illustrating an example of an X-ray irradiation method.
Figure 9:
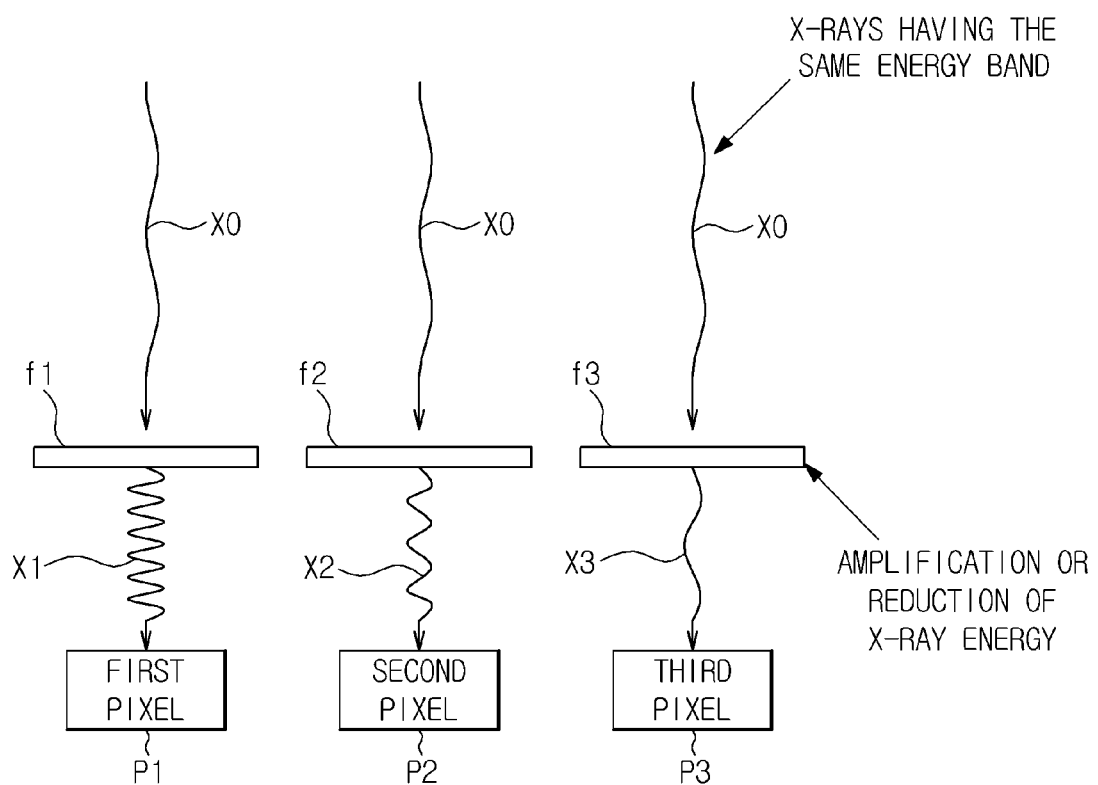
FIG. 9 is a diagram illustrating an example of a structure in which pixels detect X-rays having different energy bands through filtering.

According to another non-exhaustive example, a plurality of X-ray images may be generated, in a different manner from that of the method shown in FIGS. 7A-7C, by performing X-ray irradiation as illustrated in FIGS. 8 and 9. FIG. 8 is a diagram illustrating an example for describing an X-ray irradiation. FIG. 9 is a diagram illustrating an example of a structure in which pixels detect filtered X-rays having different energy bands. As illustrated in FIG. 8, the X-ray generator 10 irradiates X-rays to the X-ray detection panel 100. As illustrated in FIG. 9, X-rays are filtered while passing through filters f1, f2, and f3. The filters f1, f2, and f3 are connected to pixels p1, p2, and p3, respectively, of the X-ray detection panel 100. The first to third pixels p1 to p3 belong to the first to third pixel groups g1 to g3, respectively. Accordingly, each of the emitted energy bands of the X-rays is converted into another energy band. The filters, i.e., f1 to f3 may have different energy attenuation factors, and incident X-rays may be filtered such that the energy band of the X-rays is changed by each of the filters.

X-rays X0 having a predetermined energy band and emitted from the X-ray generator 10 are filtered while passing through a first filter f1 to be converted into first X-rays X1, which have an energy band different from that of the emitted X-rays X0. A first pixel p1 connected to the first filter f1 receives and detects the first X-rays X1 and converts the first X-rays X1 into electrical signals In the same manner, the emitted x-rays X0 are filtered while passing through a second filter f2 to be converted into second X-rays X2 having an energy band different from those of the emitted X-rays X0 and the first X-rays X1. A second pixel p2 connected to the second filter f2 receives and detects the second X-rays X2. Likewise, the third pixel p3 also receives third X-rays X3, which is filtered while passing through a third filter f3, and which have an energy band different from those of the X-rays X0, the first X-rays X1, and the second X-rays X2. Although not illustrated in the drawings, the X-ray detection panel 100 may further include a fourth pixel p4 and a fourth filter f4 connected to the fourth pixel p4. The fourth pixel p4 detects fourth X-rays X4 filtered while passing through the fourth filter f4.

Figure 10:
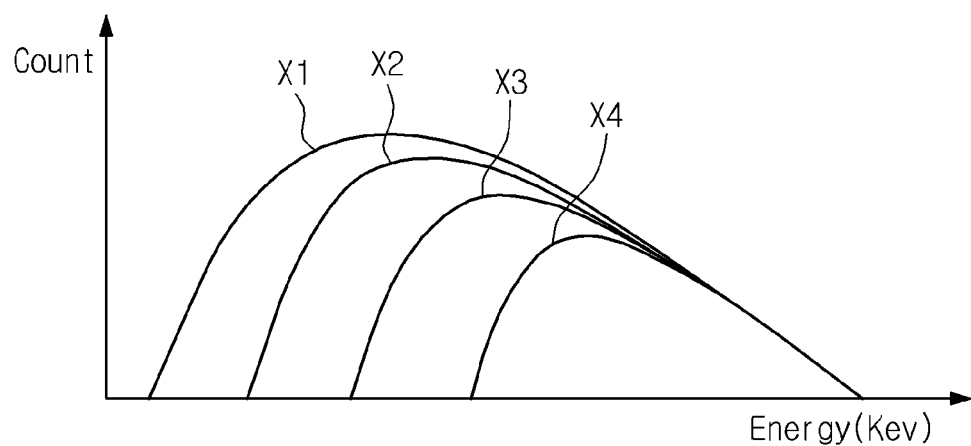
FIG. 10 is a diagram illustrating an example of energy bands of X-rays received by pixels.

FIG. 10 is a diagram illustrating an example of energy bands of X-rays received by pixels p1 to p4. The energy bands of the first to fourth X-rays X1 to X4, which have passed through the first to fourth filters f1 to f4 and are detected by the first to fourth pixels p1 to p4, may be illustrated in FIG. 10.

According to another non-exhaustive example, one of the first to fourth pixels p1 to p4 detecting the first to fourth X-rays X1 to X4, respectively, may detect the emitted X-rays X0. The filter f may not be connected to the pixels p detecting the emitted X-rays X0.

Figure 11:
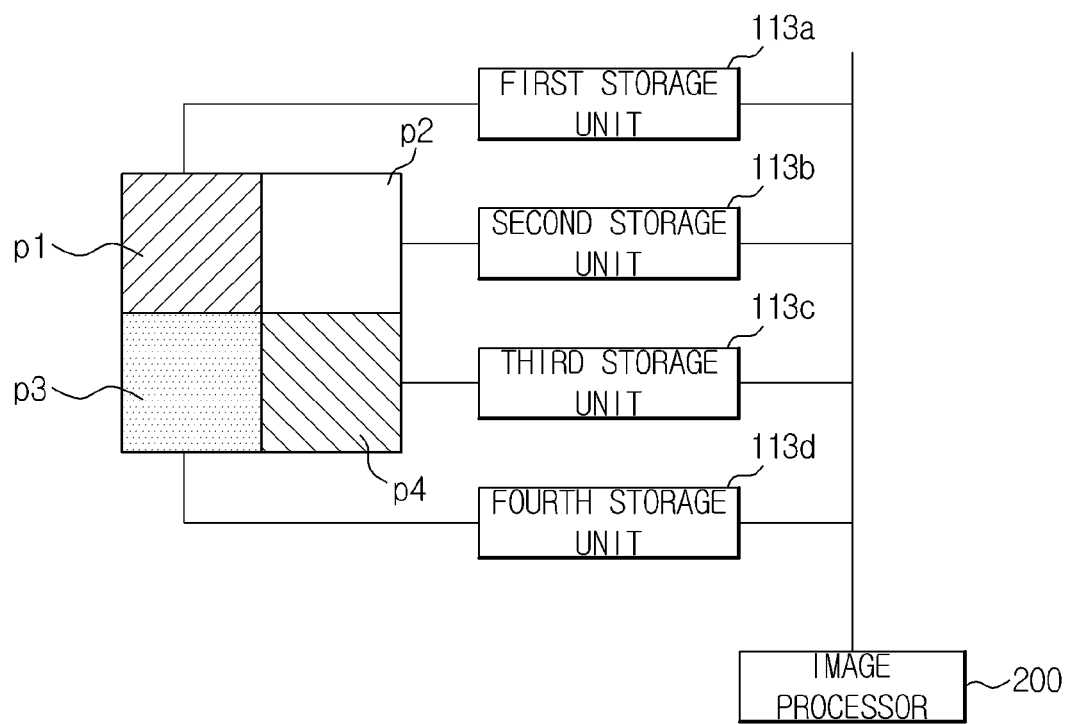
FIG. 11 is a diagram illustrating an example of a structure in which pixels are connected to storage units.

FIG. 11 is a diagram illustrating an example of a structure in which pixels are connected to storage units. As described above, the first to fourth pixels p1 to p4 detect the first to fourth X-rays X1 to X4 having different energy bands, respectively. The first to fourth pixels p1 to p4 convert the first to fourth X-rays X1 to X4 into electrical signals through the scintillator 111 and the photodiode 112 of each of the first to fourth pixels p1 to p4. The first to fourth pixels p1 to p4 store the respective electrical signals in each of their respective storage unit 113.

As illustrated in FIG. 11, the first to fourth pixels p1 to p4 may include first to fourth storage units 113a to 113d, respectively, which are electrically connected to the photodiode 112 of each of the first to fourth pixels p1 to p4. The first to fourth storage units 113a to 113d store the first to fourth electrical signals output from the photodiode 112 of each of the pixels p1 to p4, respectively. A storage unit 113 corresponding to a $k^{th}$ pixel pk refers to a $k^{th}$ storage unit 113k (k=1, 2, 3, 4 ... ).

The plurality of first storage units 113a store the electrical signals output from the plurality of first pixels p1. As illustrated in FIG. 11, the image processor 200 reads the first electrical signals from the first storage units 113a to acquire readout data to generate a first X-ray imaged based on the first electrical signals. The same process is applied to the other storage units 113b to 113d corresponding to the other pixels p2 to p4.

The image processor 200 of the X-ray imaging apparatus reads the first to fourth electrical signals from the first to fourth storage units 113a to 113d, respectively. The image processor 200 generates first to fourth X-ray images based on the first to fourth electrical signals and performs an additional image processing operation for each of the first to fourth X-ray images. According to another non-exhaustive example, the image processor 200 generates a separate image, for example, a multi-energy X-ray image, by combining the first to fourth X-ray images.

According to a non-exhaustive example, in order to generate an X-ray image, the image processor 200 reads out the electrical signals from at least one pixel group among the pixel groups g1 to g4, to acquire readout data of a portion of an X-ray image. The image processor 200 calculates estimated data of another portion of the X-ray image based on the readout data, and generates an X-ray image corresponding to X-rays having a predetermined energy band by combining the readout data and the estimated data.

Figure 12:
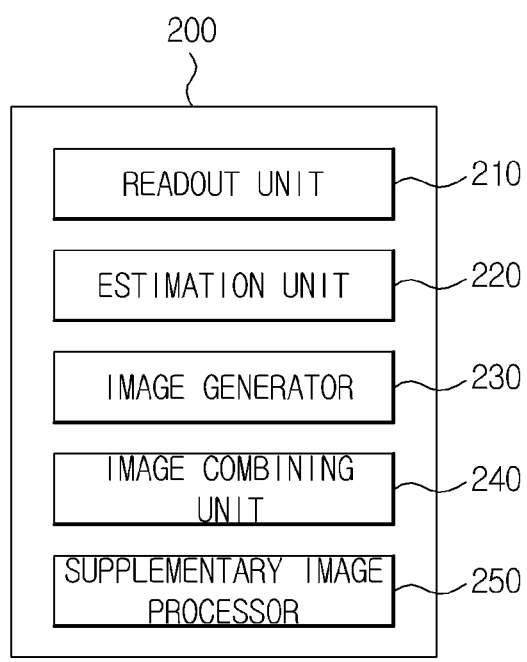
FIG. 12 is a diagram illustrating an example of an image processor.

FIG. 12 is a diagram illustrating an example of an image processor. As illustrated in FIG. 12, the image processor 200 includes a readout unit 210, an estimation unit 220, an image generator 230, an image combining unit 240, and a supplementary image processor 250. The readout unit 210 may be, for example an Readout Integrated Circuit (ROIC) circuit, which reads out the electrical signals stored in the plurality of storage units 113 of a predetermined pixel group to acquire a plurality of readout data. The estimation unit 220 calculates estimated data of other pixels of the other pixel groups based on the plurality of readout data. The image generator 230 generates an X-ray image by combining the readout data and estimated data.

The readout unit 210 reads out the electrical signals from the storage units 113 of the pixels p of a predetermined pixel group of the X-ray detection panel 100 and acquires image data from the pixels p for an X-ray image corresponding to the pixels p based on the electrical signals, i.e., readout data. According to a non-exhaustive example the readout unit 210 does not read out all electrical signals of all pixels p of the X-ray detection panel 100 but separately reads out the electrical signals in groups. In a non-exhaustive example, the readout unit 210 reads out electrical signals from some of the pixels p, for example, the plurality of first storage units 113a of the first pixel group g1 in accordance with a predetermined reference, for example, the energy band of the detected X-rays. Subsequently, the readout unit 210 sequentially reads out the second electrical signals, the third electrical signals, and the fourth electrical signals from the plurality of second storage units 113b of the second pixel group g2, the plurality of third storage units 113c of the third pixel group g3, and the plurality of fourth storage units 113d of the fourth pixel group g4, respectively.

According to another non-exhaustive example, the readout unit 210 may read out all electrical signals of all of the pixels p of the X-ray detection panel 100 at the same time. Here, the electrical signals may be classified and stored according to a predetermined reference, for example, the energy band of the detected X-rays. When the readout unit 210 reads the electrical signals of all of the pixels p of the X-ray detection panel 100 at the same time, the first electrical signals read out from the first pixel group g1 to the fourth electrical signals read out from the fourth pixel group g4 may be stored in separate storage units or additional information may be added to the readout data to distinguish the electrical signals from each other.

The readout unit 210 does not acquire all image data of the X-ray image from the X-ray detection panel 100. The readout unit 210 only acquires readout data of a portion of the X-ray image. Thus, an X-ray image generated by use of readout data acquired from a predetermined pixel group, for example, the first pixel group g1, does not include image data corresponding to pixels of the other pixel groups, for example, the second to fourth pixel groups g1 to g4. As a result, a complete X-ray image may not be generated. The estimation unit 220 calculates estimated data by use of the readout data to acquire a complete X-ray image.

When an X-ray image is generated by combining the first electrical signals read out by the readout unit 210, image data of pixels of the X-ray image corresponding to the first pixel group g1 outputting the first electrical signals are only acquired. Thus, image data of pixels of the X-ray image corresponding to the other pixels group, for example, the second to fourth pixel groups g2 to g4 are not acquired. The estimation unit 220 acquires the image data of pixels of the X-ray image corresponding to the other pixels group, for example, the second to fourth pixel groups g2 to g4, i.e., using a plurality of readout data acquired from the plurality of first electrical signals read out from the first pixel group g1.

According to a non-exhaustive example, the estimation unit 220 may acquire the estimated data through interpolation based on readout data of two adjacent pixels. For example, the estimated data may be acquired by calculating a mean or median value between readout data of the two adjacent pixels.

The image generator 230 generates a final X-ray image by combining the readout data and the estimated data acquired. The image generator 230 may generate a plurality of X-ray images depending on the number of pixel groups. For example, the image generator 230 may generate four X-ray images corresponding to each of the pixel groups g1 to g4.

The image processor 200 may further include an image combining unit 240. The image combining unit 240 may combine a plurality of X-ray images, for example, the first to fourth X-ray images generated by the image generator 230 to generate a multi-energy X-ray image. As described above, since the pixel groups, for example, the first to fourth pixel groups g1 to g4 detect X-rays having different energy bands, the first to fourth X-ray images are X-ray images generated using X-rays having different energy bands. Thus, a multi-energy X-ray image using X-rays having four energy bands may be acquired by combining the first to fourth X-ray images.

The image processor 200 may further include a supplementary image processor 250. The supplementary image processor 250 may apply predetermined image processing to the plurality of X-ray images generated by the image generator 230 to generate a variety of X-ray images. In addition, the supplementary image processor 250 may add a predetermined weight to each of the plurality of images before the images are combined by the image combining unit 240. Alternatively, the supplementary image processor 250 may apply energy subtraction to the plurality of X-ray images to obtain an energy subtraction X-ray image in which soft tissues are separately illustrated.

According to another non-exhaustive example, a color X-ray image may be generated by coloring the acquired X-ray images.

Elements of the image processor 200 generate at least one X-ray image in substantially the same manner as described above.

Figure 13:
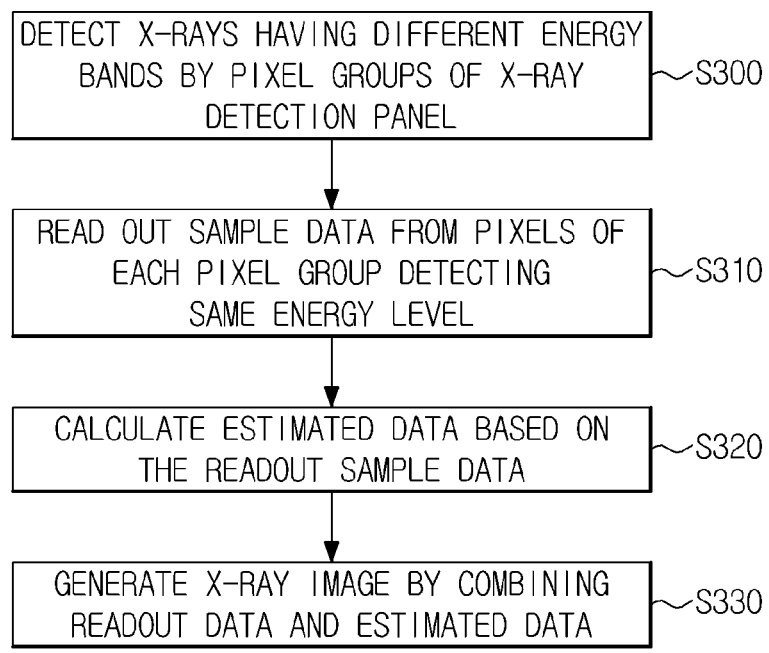
FIG. 13 is a diagram illustrating an example of a method of generating an X-ray image.

FIG. 13 is a diagram illustrating an example of a method of generating an X-ray image. The operations in FIG. 13 may be performed in the sequence and manner as shown, although the order of some operations may be changed or some of the operations omitted without departing from the spirit and scope of the illustrative examples described. Many of the operations shown in FIG. 13 may be performed in parallel or concurrently. The description of FIGS. 1-12 is also applicable to FIG. 13, and thus will not be repeated here.

In S300, the pixel groups, for example, pixel groups g1 to g4 of an X-ray detection panel 100 detect X-rays having different energy bands. In S310, a plurality of readout data are acquired from pixels, for example, pixels p1 to p4, of each of the pixel groups g1 to g4. In S320, a plurality of estimated data is calculated based on the plurality of readout data. In S320, an X-ray image is generated by combining the readout data and the estimated data.

Figure 14:
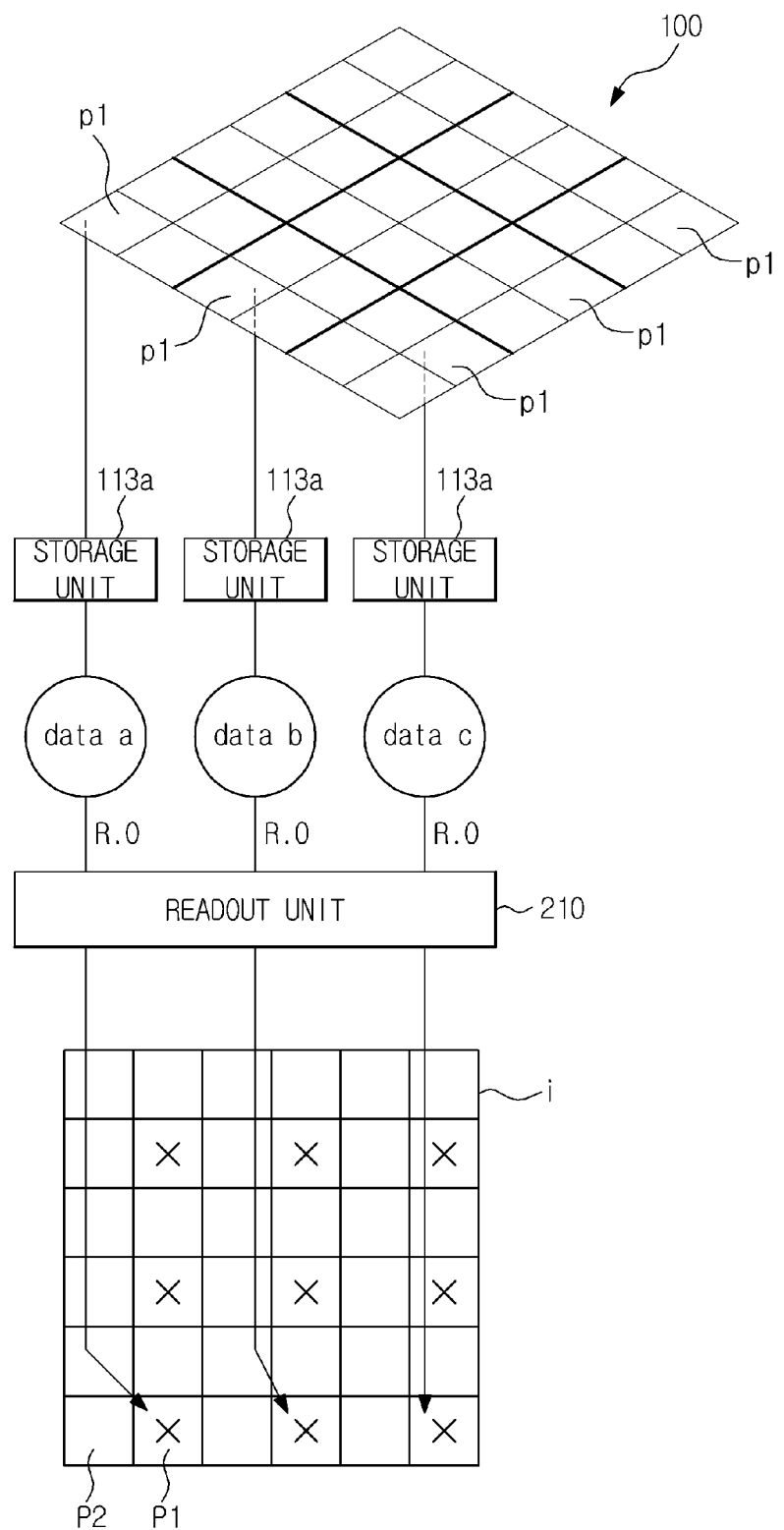
FIGS. 14 to 16 are diagrams illustrating examples for describing a method of generating an X-ray image.
Figure 15:
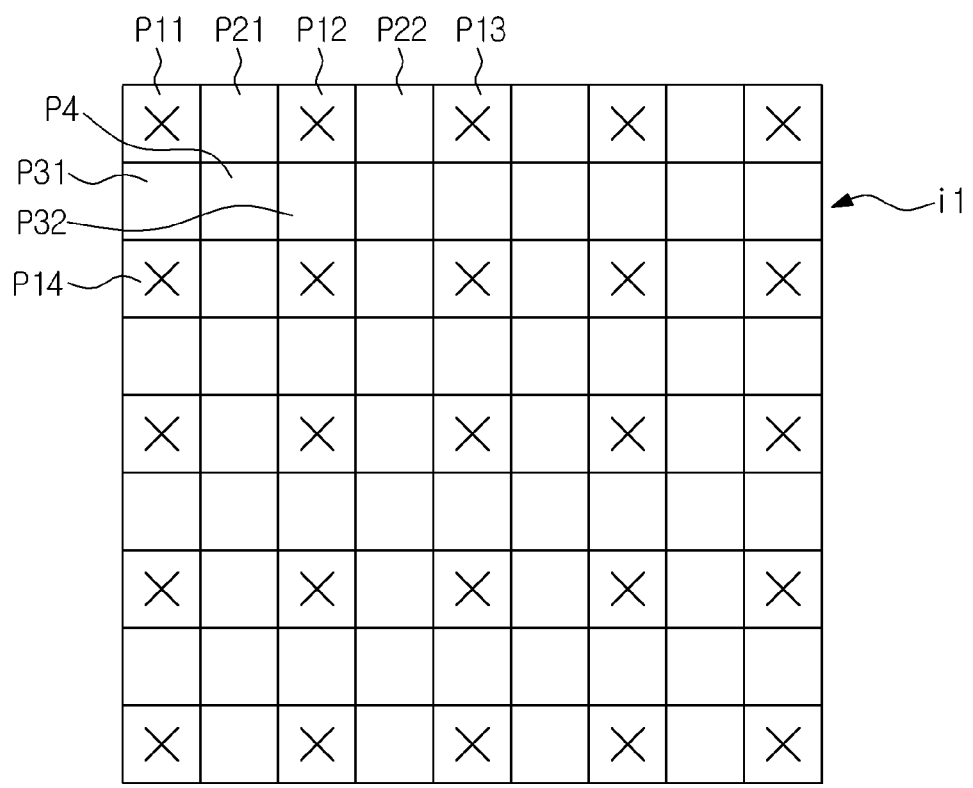
Figure 16:
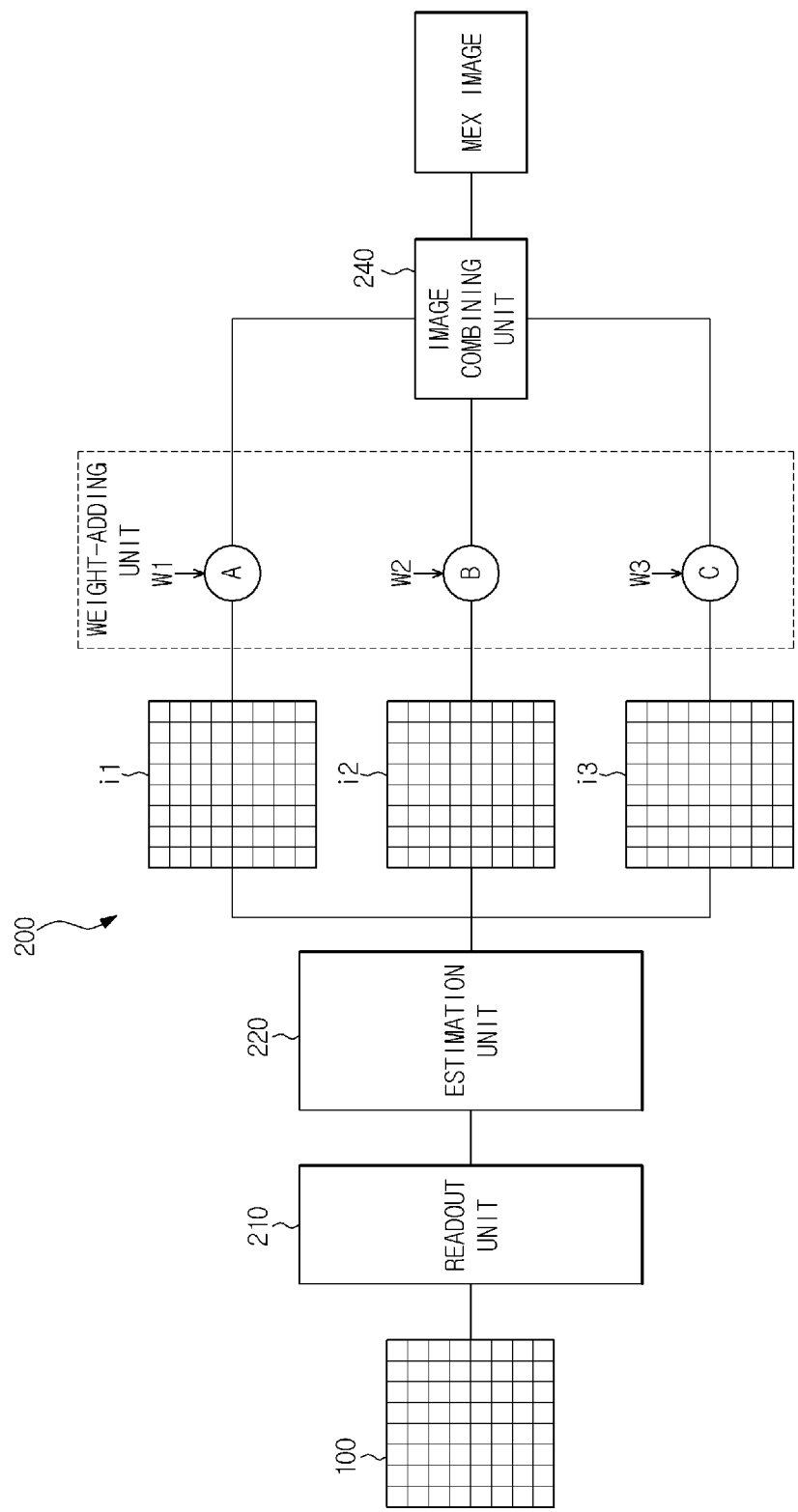

FIGS. 14 to 16 are diagrams illustrating examples for describing the method of generating an X-ray image. As illustrated in FIG. 14, the X-ray detection panel 100 includes a plurality of pixel groups g1 to g4. As described above, each of the pixel groups g1 to g4 includes a plurality of pixels p. The plurality of pixels belonging to each of the pixel groups g1 to g4, for example, first pixels p1 of the first pixel group g1, are designed to detect X-rays having a predetermined energy band. As described above and illustrated in FIG. 2, each of the first pixels p1 may be provided with a first filter f1 that attenuates the energy band of the X-rays, such that the first pixel p1 may detect X-rays having a predetermined energy band. The first filter f1 has an energy attenuation factor different from those of second to fourth filters f2 to f4 applied to the second to fourth pixels p2 to p4, respectively.

With reference to FIGS. 13 and 14, in S300, when X-rays are irradiated to the X-ray detection panel 100 having the first pixel group g1, including the first pixels p1, that are provided with the first filters f1, the first pixels p1 of the first pixel group g1 detect X-rays having the predetermined energy band attenuated through the first filters f1 and convert the X-rays into a plurality of first electrical signals. As shown in FIG. 14, the converted first electrical signals are stored in a plurality of storage units 113a.

With reference to FIGS. 13 and 14, in S310, the readout unit 210 of the image processor 200 acquires first readout data, data a to data c, from each of the storage units 113a. Likewise, the readout unit 210 acquires readout data for pixels p1 to p4 of each of the pixel groups g1 to g4.

As shown in a lower portion of FIG. 14, readout data of a location or region P1 of an X-ray image i may be acquired (portion marked with 'X' in FIG. 14) by acquiring data a from storage unit 113a. However, data of another portion of the X-ray image i, for example, a region P2 not marked with 'X' in FIG. 14, may correspond to the second to fourth electrical signals and may not be acquired at this time. Other pixels of the X-ray detection panel 100 except for the first pixels p1, for example, the second to fourth pixels p2 to p4, detect X-rays having energy bands different from that of the first pixel p1 and convert the X-rays into second to fourth electrical signals, respectively. To obtain data for region P2 not marked with 'X' in a lower matrix of FIG. 14, in S320, the estimation unit 220 of the image processor 200 calculates estimated data by use of the first readout data acquired from the first pixels p1.

FIG. 15 illustrates an example of a first X-ray image i1, which corresponds to the first pixel group g1. The first X-ray image i1 is acquired when the X-ray detection panel 100 includes, for example, four pixel groups, i.e., the first to fourth pixel groups g1 to g4. As illustrated in FIG. 15, according to a non-exhaustive example, readout data of predetermined positions of an X-ray image having a predetermined energy band is acquired from the first storage units 113a of the first pixel group g1. These regions correspond to the regions marked with 'X' in FIG. 15, and include regions P11 to P14. Estimated data of a region not having readout data and disposed between regions having readout data, may be estimated through interpolation. For example, the estimated data of region P21, which is disposed between regions P11 and P12, may be estimated using readout data of regions P11 and P12. The estimated data may be calculated based on a median or mean value between readout data of regions P11 and P12. Likewise, estimated data of region P22 may be calculated through interpolation using readout data of regions P12 and P13, and estimated data of region P31 may also be calculated through interpolation using readout data of regions P11 and P14.

Estimated data of a region not having readout data and disposed below and between P21 and P22, for example region P32, is calculated based on estimated data of regions P21 and P22 through, for example, interpolation. As another non-exhaustive example, the estimated data of region P32 may be calculated, through interpolation, using the readout data of P12 and the readout data of the region marked with an 'X' directly below P32 and between readout data of regions P21 and P22. As another non-exhaustive example, the estimated data of region P32 may be calculated, through interpolation, based on a median or mean value of P21, P22, P12, and the region marked with an 'X' directly below P32.

Likewise, the estimated data for P4 may be calculated based on readout data of regions P11 and P12 through, for example, interpolation. As another non-exhaustive example, the estimated data of region P4 may be calculated, through interpolation, using the estimated data of P31 and P32. The examples for calculating estimated data described above are only non-exhaustive illustrations of some of the interpolation that may be used, and other interpolations using different combination of regions are considered to be well within the scope of the present disclosure. The interpolation may include, but is not limited to, calculating the median or mean value of the readout and/or the estimated data.

In S330, the calculated estimated data is regarded as image data of regions, where the readout data is not acquired, e.g., regions P21, P22, P32, P31, and P4. The plurality of acquired readout data and the plurality of estimated data are combined to generate a final X-ray image, for example, a first X-ray image i1. The above-described process is repeated for the other second to fourth pixel groups g2 to g4. A plurality of X-ray images, e.g., first to fourth X-ray images i1 to i4 may be acquired as illustrated in FIGS. 2 and 16 (image i4 is not illustrated in these non-exhaustive examples).

As illustrated in FIG. 16, a plurality of X-ray images, for example, first to third X-ray images i1 to i3, corresponding to a plurality of pixel groups, for example, the first to third pixels groups g1 to g3, of a single X-ray detection panel 100 may be acquired by acquiring a plurality of readout data from the pixel groups g1 to g3 and calculating estimated data from the readout data. In other words, the X-ray detection panel 100 is de-mosaiced to acquire a plurality of X-ray images i1 to i3, and a plurality of X-ray images i1 to i3 may be acquired by performing X-ray irradiation once. As shown in FIG. 16, a contrast or brightness of the X-ray images i1 to i3 is controlled by adding a predetermined energy weight w1 to w3, respectively, to the generated X-ray images. Such energy weight may be determined according to the energy band of the first X-rays or by an X-ray image user. The weighted X-ray images may be combined to obtain a final multi-energy X-ray image.

Figure 17:
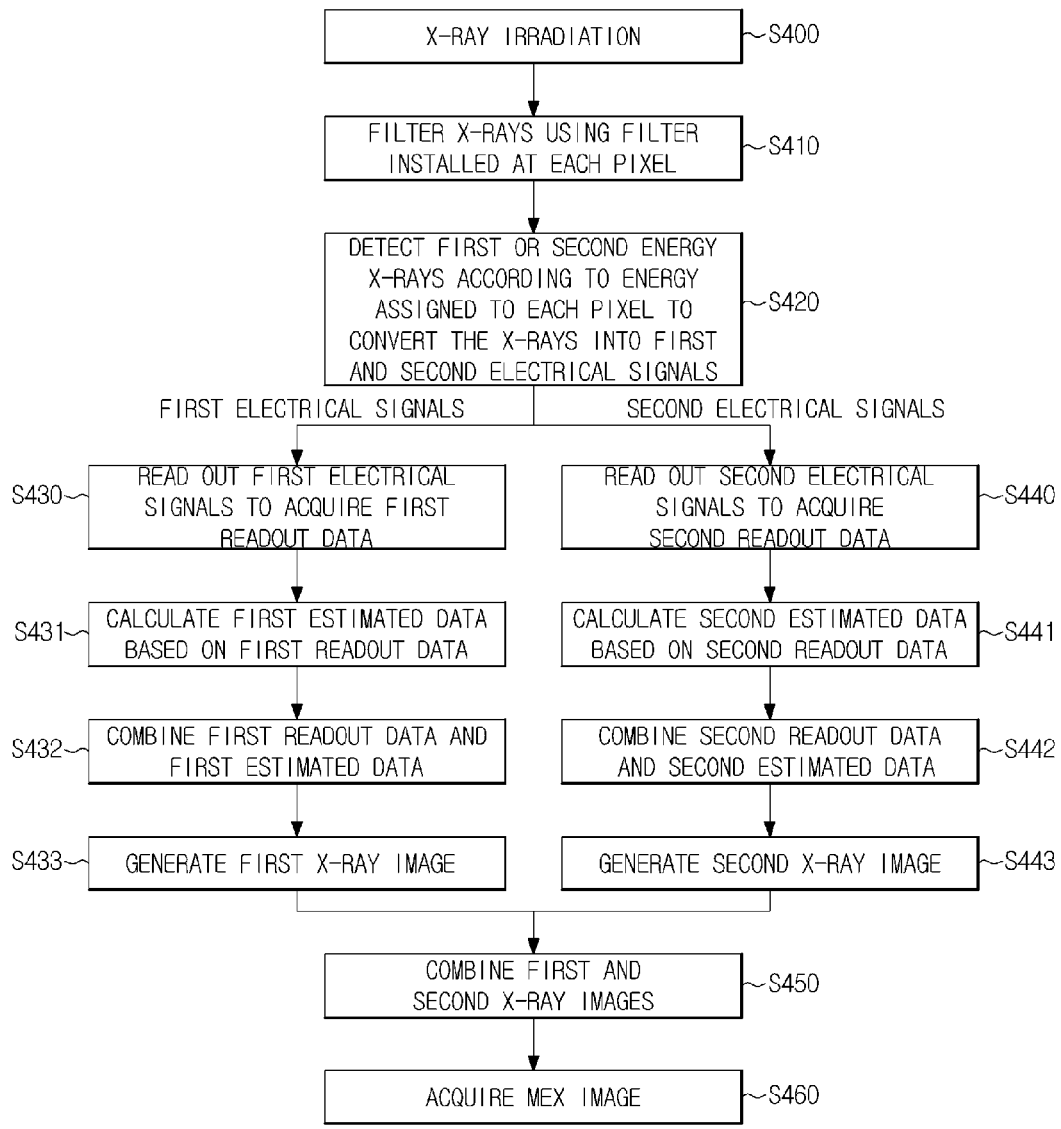
FIGS. 17 to 20 are diagrams illustrating examples of methods of generating X-ray images.

FIG. 17 is a diagram illustrating an example of a method of generating an X-ray image. The operations in FIG. 17 may be performed in the sequence and manner as shown, although the order of some operations may be changed or some of the operations omitted without departing from the spirit and scope of the illustrative examples described. Many of the operations shown in FIG. 17 may be performed in parallel or concurrently. The description of FIGS. 1-16 is also applicable to FIG. 17, and thus will not be repeated here.

In S400, an object is irradiated with X-rays in order to generate an X-ray image. An X-ray detection panel 100 receives X-rays that have passed through the object ob. In S410, filters, for example, first and second filters f1 and f2, filter the X-rays. As described above, the first and second filters f1 and f2 change the energy bands of the incident X-ray and are installed at first pixels p1 of the first pixel group g1 and second pixels p2 of the second pixel group g2. In S420, the pixels, for example, the first pixels p1 and the second pixels p2 respectively detect X-rays having different energy bands according to energy band assigned to the filters and convert the detected X-rays into first and second electrical signals.

As explained above, the readout unit 210 of the image processor 200 detects and reads the first and second electrical signals. For example, in S430, the readout unit 210 reads out the first electrical signals to acquire first readout data to acquire image data of a portion of a first X-ray image. In S431, an estimation unit 220 of the image processor 200 calculates first estimated data based on the first readout data to acquire image data of another portion of the first X-ray image. In S432, the first readout data and the first estimated data are combined to generate a final first X-ray image in S433. The second electrical signals goes through a similar process in S440 to S443.

In S450, the image combining unit 240 of the image processor 200 combines the first X-ray image and the second X-ray image to generate a final multi-energy X-ray (MEX) image in S460. Accordingly, a multi-energy X-ray image may be acquired by performing X-ray irradiation once.

Figure 18:
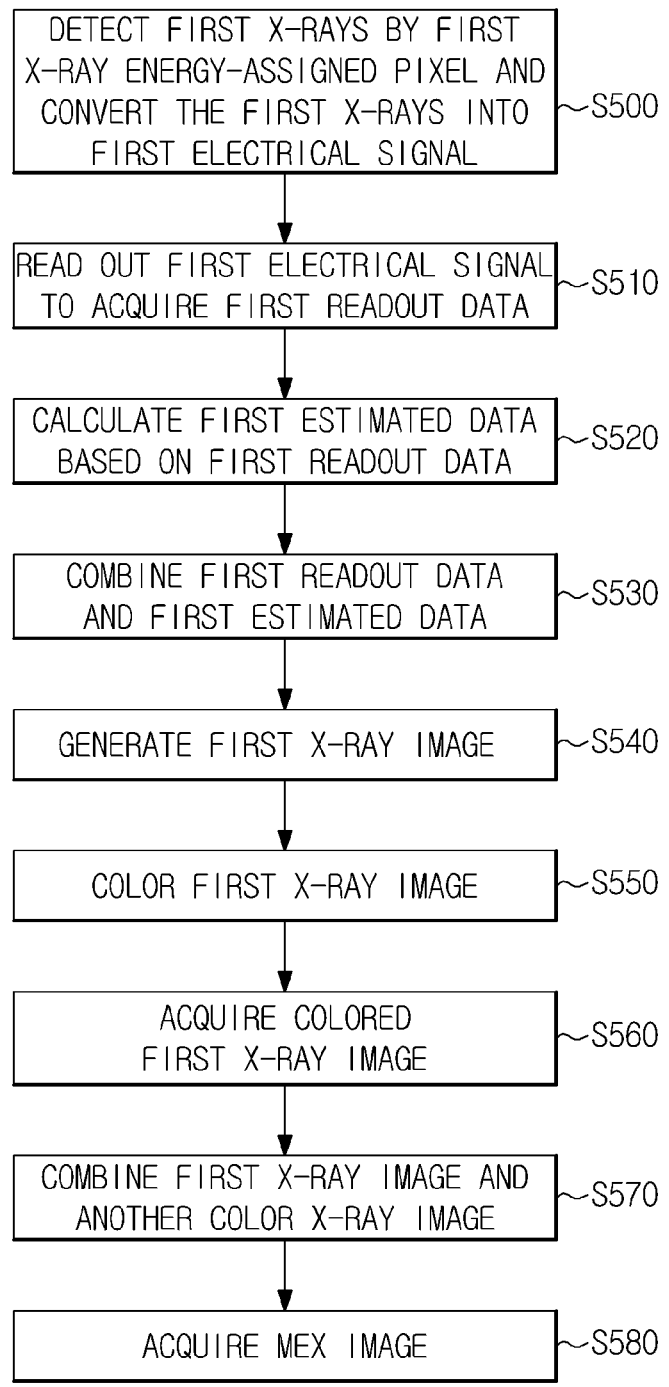

FIG. 18 is a diagram illustrating an example of a method of generating an X-ray image. The operations in FIG. 18 may be performed in the sequence and manner as shown, although the order of some operations may be changed or some of the operations omitted without departing from the spirit and scope of the illustrative examples described. Many of the operations shown in FIG. 18 may be performed in parallel or concurrently. The description of FIGS. 1-17 is also applicable to FIG. 18, and thus will not be repeated here.

Referring to FIG. 18, the method of generating an X-ray image enables acquisition of a color multi-energy X-ray image. In S500, an object is irradiated with X-rays in the same manner as described above. A pixel group of an X-ray detection panel 100 detecting a first X-ray energy, for example, a first pixel p1 of a first pixel group g1, detects first X-rays and converts the first X-rays into first electrical signals.

In S510, as described above, first readout data is acquired from the first electrical signal. In S520, the first estimated data is calculated and acquired based on the first readout data.

In S530 and S540, a complete first X-ray image is generated by combining the first readout data and the first estimated data.

In S550, the first X-ray image may be colored by adding colors having predetermined RGB values to the first X-ray image, for example, tissues shown in the first X-ray image, based on characteristics of the tissues or resolution of the detected tissues (colorization, S550). In S560, a color first X-ray image is acquired.

A second X-ray image acquired from second X-rays detected by another pixel group, for example, the second pixel p2 of the second pixel group g, may also be colored by the method described above.

In S570 and S580, a plurality of color X-ray images may be acquired and combined to generate a color multi-energy X-ray image.

Figure 19:
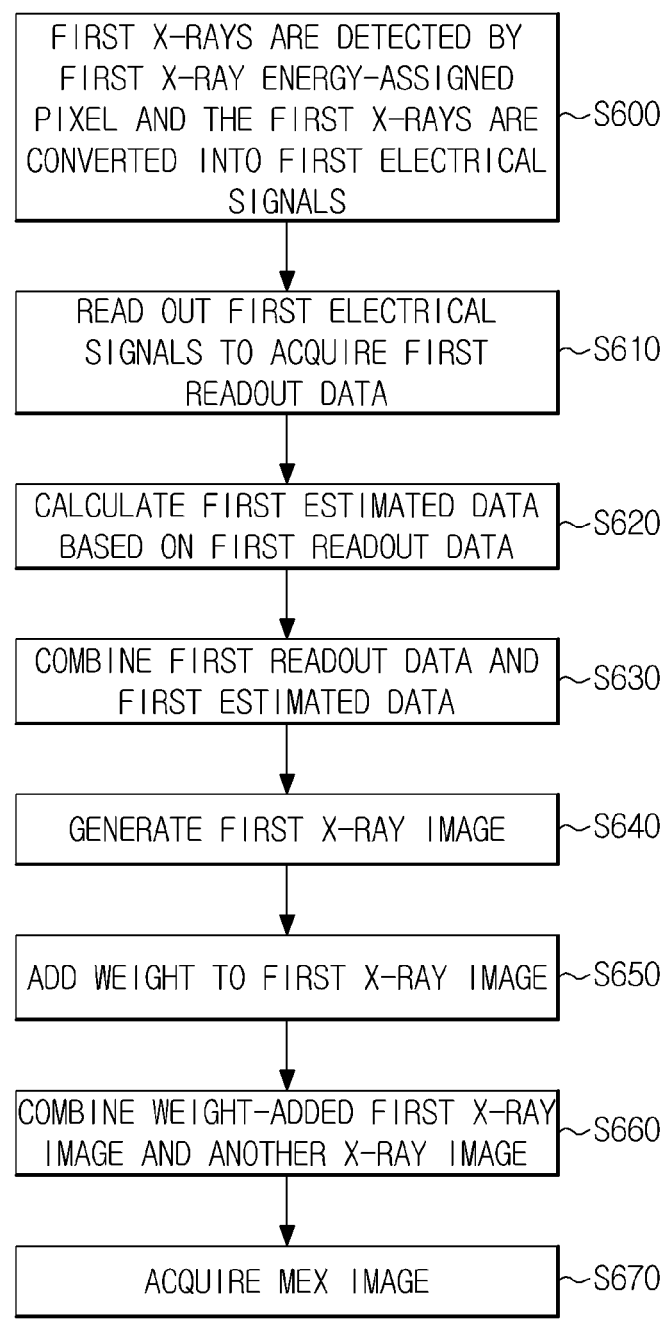

FIG. 19 is a diagram illustrating an example of a method of generating an X-ray image. The operations in FIG. 19 may be performed in the sequence and manner as shown, although the order of some operations may be changed or some of the operations omitted without departing from the spirit and scope of the illustrative examples described. Many of the operations shown in FIG. 19 may be performed in parallel or concurrently. The description of FIGS. 1-18 is also applicable to FIG. 19, and thus will not be repeated here. As illustrated in FIG. 19, a multi-energy X-ray image with additional predetermined weight may be acquired.

In S600, as described above, the first pixels p1 of the first pixel group g1 detect first X-rays and convert the first X-rays into first electrical signals.

In S610, the image processor 200 reads out the first electrical signals to acquire first readout data. In S620, the image processor calculates first estimated data based on the first readout data. In S630, the image processor combines the first readout data and the first estimated data to generate a first X-ray image in S640.

In S650, contrast or brightness of the first X-ray image is controlled by adding a predetermined energy weight to the generated first X-ray image. Such energy weight may be determined according to the energy band of the first X-rays or by an X-ray image user.

Likewise, weight may be added to another X-ray image, for example, a second X-ray image, and a plurality of X-ray images to which predetermined weights are added may be acquired. In S660, the first weighted X-ray image is combined with another X-ray image, for example, the second weighted X-ray image to obtain a final multi-energy X-ray image in S670. In another non-exhaustive example, first weighted X-ray image is combined with another X-ray image, for example, the second weighted X-ray image to which the weight is not added to obtain a final multi-energy X-ray image in S670. Thus, an image having a high contrast to noise rate (CNR) may be obtained by adjusting the weight added to each X-ray image.

Figure 20:
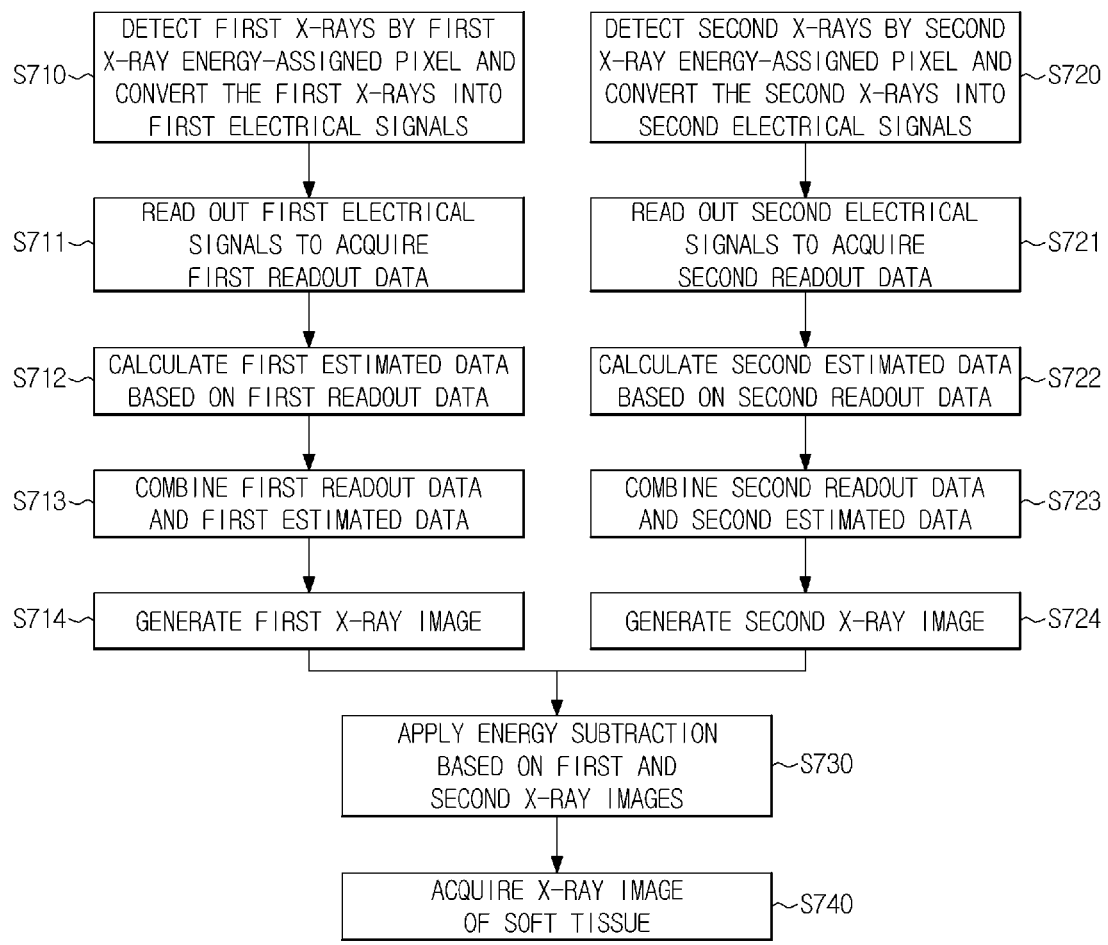

FIG. 20 is a diagram illustrating an example of a method of generating an X-ray image. The operations in FIG. 20 may be performed in the sequence and manner as shown, although the order of some operations may be changed or some of the operations omitted without departing from the spirit and scope of the illustrative examples described. Many of the operations shown in FIG. 20 may be performed in parallel or concurrently. The description of FIGS. 1-19 is also applicable to FIG. 20, and thus will not be repeated here. Referring to FIG. 20, a multi-energy X-ray image only illustrating soft tissues from which hard tissues such as bones are removed may be acquired by performing X-ray irradiation once. As described above, in S710 to S714 and S720 to S724 a first X-ray image and a second X-ray image, respectively, may be acquired by use of first X-rays and second X-rays by combining the readout data and the estimated data for the first X-ray image and the second X-ray image.( )

In a non-exhaustive example only, the first X-ray image is acquired using X-rays having a low energy band, and the second X-ray image is acquired using X-rays having a high energy band. In other words, the first X-ray image is acquired by use of X-rays that have passed through filters having a high energy attenuation factor, and the second X-ray image is acquired by use of X-rays that have passed through filters having a low energy attenuation factor.

In S730, energy subtraction is applied to the acquired first and second X-ray images to obtain image data of soft tissues from which hard tissues such as bones are removed in S740.

Intensities of signals of the X-ray image acquired using X-rays having the low energy band, i.e., the first X-ray image, and the X-ray image acquired using X-rays having the high energy band, i.e., the second X-ray image, are shown in Table 1 below.

TABLE 1

|  | First soft tissue | Second soft tissue | Bone |
| --- | --- | --- | --- |
| Low energy band | 30 | 40 | 100 |
| High energy band | 24 | 30 | 50 |
| High energy band X 2 | 48 | 60 | 100 |
| Row 3-row 1 | 18 | 20 | 0 |

Table 1 shows examples of signal intensities for soft tissues assuming that the signal intensity for bones is 100 in the X-ray image acquired using the first X-rays, i.e., the low energy band X-rays. As shown in rows 1 and 2, signal intensities for bones are considerably different between the X-ray image using the low energy band X-rays and that using the high energy band X-rays, but the signal intensities for other soft tissue do not vary as much. In row 3 of Table 1, the high energy band is multiplied by 2, and a difference between rows 1 and 3 (subtraction) is calculated to obtain values listed in row 4. As shown in column 4 and row 4 of Table 1, the signal value for bones is 0 by this operation, i.e. the data of the bones is removed. As a result, an X-ray image illustrating only soft tissues may be acquired.

Since a variety of multi-energy X-ray images may be acquired by performing a small number of X-ray irradiations or by performing X-ray irradiation once, the object need not be exposed to X-rays plural times. Accordingly, multiple exposure of a human body to X-rays may be avoided. Moreover, image deterioration caused by movement of a patient or tissues thereof during a plurality of X-ray irradiations may be reduced. As a result, quality of the multi-energy X-ray image may be improved.

In addition, a breast compression time may also be reduced in X-ray imaging of a breast using an FFEM apparatus so that pain caused by compression of the breast may be reduced.

As described above, an X-ray detection panel, an X-ray image generating module, an X-ray imaging apparatus, and a method of generating an X-ray image are provided. Accordingly, a plurality of X-ray images of various energy bands may be acquired without performing X-ray irradiation plural times.

X-rays having a plurality of energy bands may be simultaneously detected by use of a single X-ray detection panel. Thus, the X-ray image generating module may acquires a plurality of X-ray images corresponding to X-rays having the plurality of energy bands detected by the X-ray detection panel. Thus, a user of the X-ray image, for example, a doctor, may diagnose or confirm internal tissues, structures, or contents of a subject to be diagnosed more accurately using the X-ray image.

The methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein.

The apparatuses and units described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An X-ray imaging apparatus comprising:
 an X-ray generator configured to emit X-rays;
 an X-ray detection panel comprising a plurality of pixel groups, each pixel group configured to detect X-rays having an energy band and to convert the detected X-rays into electrical signals;
 a plurality of storage elements provided in correspondence to each pixel group and store the electrical signal from each pixel group respectively; and
 an image processor configured to acquire readout data from the electrical signals of at least one of the plurality of pixel groups, stored in the at least one of the storage elements, to calculate estimated data, and to generate an X-ray image by combining the readout data and the estimated data.

2. The X-ray imaging apparatus of claim 1, wherein the image processor is further configured to generate a color X-ray image by adding colors having a predetermined RBG values to the X-ray image.

3. The X-ray imaging apparatus of claim 1, wherein the image processor is configured to acquires an image having a high contrast to noise rate (CNR) by adding a weight to the generated X-ray image.

4. The X-ray imaging apparatus of claim 1, wherein the image processor is configured to generate a plurality of X-ray images corresponding to the electrical signals of a plurality of pixel groups.

5. The X-ray imaging apparatus of claim 4, wherein the image processor is configured to generate energy subtraction X-ray images by applying energy subtraction to the plurality of X-ray images.

6. The X-ray imaging apparatus of claim 4, wherein the image processor is configured to generate a multi-energy X-ray image by combining the generated plurality of X-ray images.

7. The X-ray imaging apparatus of claim 1,
 wherein: the X-ray detection panel further comprises a plurality of filters disposed on a surface of pixels of the pixel groups;
 the filters are configured to adjust the energy band of the X-ray detected by the pixel groups; and
 the filters disposed over pixels of the same pixel group are configure to adjust the energy band by an identical amount.

8. The apparatus of claim 1, wherein the readout data is image data for a first portion of the X-ray image and the estimated data is image data for a second portion of the X-ray image.

9. An X-ray image generating apparatus comprising:
 an X-ray detection panel comprising a plurality of pixel groups, each pixel group configured to detect X-rays having an energy band and to convert the detected X-rays into electrical signals;
 a plurality of storage elements provided in correspondence to each pixel group and store the electrical signal from each pixel group respectively; and
 an image processor configured to acquire readout data of a first portion of an X-ray image from the electrical signals of at least one of the plurality of pixel groups, stored in the at least one of the storage elements, to calculate estimated data of a second portion of the X-ray image based on the acquired readout data, and to generate the X-ray image having a single energy band by combining the readout data and the estimated data.

10. The X-ray image generating apparatus of claim 9, wherein the image processor is further configured to generate a color X-ray image by adding colors to the generated X-ray image.

11. The X-ray image generating apparatus of claim 9, wherein the image processor is further configured to generate a contrast to noise rate (CNR) image having a high CNR by adding a weight to the generated X-ray image.

12. The X-ray image generating apparatus of claim 9, wherein the image processor is further configured to generate a plurality of X-ray images corresponding to X-rays detected by the plurality of pixel groups.

13. The X-ray image generating apparatus of claim 12, wherein the image processor is further configured to generate an energy subtraction X-ray image by applying energy subtraction to the plurality of X-ray images.

14. The X-ray image generating apparatus of claim 12, wherein the image processor is further configured to generate a multi-energy X-ray image by combining the generated plurality of X-ray images.

15. The X-ray image generating apparatus of claim 9, further comprising a plurality of filters connected to pixels of each of the pixel groups and configured to adjust energy bands of the X-rays.

16. The X-ray image generating apparatus of claim 9, wherein the estimated data is calculated based on the readout data through interpolation.

17. A method of generating an X-ray image, the method comprising:
 X-ray detection panel comprising a plurality of pixel groups, each pixel group configured to detect X-rays converting the detected X-rays into electrical signals;
 storing, by a plurality of storage elements, the electrical signals output from the plurality of pixel group respective, wherein the a plurality of storage elements correspond to the plurality of pixel group respectively;
 acquiring readout data of a first portion of an X-ray image from the electrical signals of one of the plurality of pixel groups;
 calculating estimated data of a second portion of the X-ray image based on the readout data; and
 combining the readout data and the estimated data to generate the X-ray image having a single energy band.

18. The method of claim 17, further comprising generating a color X-ray image by adding colors to the generated X-ray image.

19. The method of claim 17, further comprising generating a contrast to noise rate (CNR) image having a high CNR by adding a weight to the generated X-ray image.

20. The method of claim 18, further comprising generating a plurality of X-ray images by repeating the acquiring of the readout data, the calculating of the estimated data, and the combining the readout data and the estimated data for each of the X-rays detected by the plurality of pixel groups.

21. An X-ray image generating apparatus comprising:
 an X-ray detection panel comprising a plurality of pixel groups, each pixel group configured to detect X-rays having an energy band and to convert the detected X-rays into electrical signals;
 a plurality of filters disposed on a surface of pixels of the pixel groups and the filters are configured to adjust the energy band of the X-ray detected by each pixel group by an identical amount;

a plurality of storage elements provided in correspondence to each pixel group and store the electrical signal from each pixel group respectively; and an image processor configured to acquire readout data from the electrical signals of at least one of the plurality of pixel groups, stored in the at least one of the storage elements, to calculate estimated data, and to generate an X-ray image by combining the readout data and the estimated data.

22. The X-ray image generating apparatus of claim 21, wherein the pixel groups are sequentially disposed in the X-ray detection panel.

* * * * *